United States Patent
Hovland et al.

(10) Patent No.: US 11,154,414 B2
(45) Date of Patent: Oct. 26, 2021

(54) APPARATUS AND METHODS FOR TREATING VENOUS OCCLUSIVE DISORDERS

(71) Applicant: NuGyn, Inc., Northfield, MN (US)

(72) Inventors: Claire Hovland, Northfield, MN (US); Curtis Olson, St. Paul, MN (US)

(73) Assignee: NuGyn, Inc., Northfield, MN (US)

( * ) Notice: Subject to any disclaimer, the term of this patent is extended or adjusted under 35 U.S.C. 154(b) by 324 days.

(21) Appl. No.: 16/411,231

(22) Filed: May 14, 2019

(65) Prior Publication Data

US 2019/0350745 A1 Nov. 21, 2019

Related U.S. Application Data

(60) Provisional application No. 62/672,017, filed on May 15, 2018.

(51) Int. Cl.
*A61F 5/41* (2006.01)
*A61H 19/00* (2006.01)

(52) U.S. Cl.
CPC .......... *A61F 5/41* (2013.01); *A61F 2005/412* (2013.01); *A61F 2005/414* (2013.01); *A61H 19/32* (2013.01)

(58) Field of Classification Search
CPC . A61F 5/41; A61F 2005/412; A61F 2005/414
USPC ..................................... 600/38–41
See application file for complete search history.

(56) References Cited

U.S. PATENT DOCUMENTS

| | | | |
|---|---|---|---|
| 4,175,554 A | 11/1979 | Gerow | |
| 4,671,262 A | 6/1987 | West | |
| 4,718,411 A | 1/1988 | Stewart | |
| 4,741,329 A | 5/1988 | Marcune | |
| 5,020,522 A * | 6/1991 | Stewart | A61F 5/41 600/38 |
| 5,094,230 A | 3/1992 | Clark, Jr. | |
| 5,115,800 A | 5/1992 | Matejevic et al. | |
| 5,125,890 A * | 6/1992 | Merrill | A61F 5/41 600/39 |
| 5,195,943 A | 3/1993 | Chaney | |
| 5,344,389 A | 9/1994 | Walsdorf et al. | |
| 5,421,808 A * | 6/1995 | Osbon | A61F 5/41 600/38 |
| 5,462,514 A | 10/1995 | Harris | |

(Continued)

OTHER PUBLICATIONS

Cezar, Christine et al., Biologic-free mechanically induced muscle regeneration, PNAS (Feb. 9, 2016);113(6):1534-1539.

(Continued)

*Primary Examiner* — Samuel G Gilbert
(74) *Attorney, Agent, or Firm* — Karrie Gemignani Weaver; Weaver Legal and Consulting LLC

(57) ABSTRACT

Apparatus, methods and systems for treating venous occlusive disease are provided. Generally, devices include a soft extension member that is adapted to be mounted at a proximal end of a therapeutic vacuum device. The soft extension member includes a proximal end composed of a tissue contacting portion configured to receive a tissue to be treated, and a distal end composed of a collar configured to be mounted onto an exterior surface of a vacuum chamber. Apparatus, methods and systems for increasing clitoral and cavernosal tumescence by application of a vacuum are also provided.

8 Claims, 4 Drawing Sheets

SECTION A-A

(56) References Cited

U.S. PATENT DOCUMENTS

| | | | |
|---|---|---|---|
| 5,590,764 A | 1/1997 | Wood | |
| 5,624,378 A | 4/1997 | Baldecchi | |
| 5,669,869 A | 9/1997 | Strom | |
| 5,683,383 A | 11/1997 | Russell et al. | |
| 5,707,341 A | 1/1998 | Mathewuse | |
| 5,713,830 A | 2/1998 | Tucker et al. | |
| 5,836,864 A | 11/1998 | Clark, Jr. | |
| 5,895,356 A | 4/1999 | Andrus et al. | |
| 5,921,914 A | 7/1999 | Tucker et al. | |
| 6,015,393 A | 1/2000 | Hovland et al. | |
| 6,030,318 A | 2/2000 | Howard | |
| 6,036,635 A | 3/2000 | Altshuler | |
| 6,099,463 A * | 8/2000 | Hockhalter | A61H 19/34 600/38 |
| 6,149,667 A | 11/2000 | Hovland et al. | |
| 6,169,914 B1 | 1/2001 | Hovland et al. | |
| 6,183,414 B1 * | 2/2001 | Wysor | A61B 5/14551 600/38 |
| D443,057 S | 5/2001 | Hovland et al. | |
| 6,231,502 B1 | 5/2001 | McCarty | |
| 6,248,059 B1 | 6/2001 | Gamper et al. | |
| 6,251,076 B1 | 6/2001 | Hovland et al. | |
| 6,277,052 B1 | 8/2001 | Howard | |
| D449,690 S | 10/2001 | Hovland et al. | |
| 6,458,073 B1 | 10/2002 | Bonthuys | |
| 6,464,653 B1 | 10/2002 | Hovland et al. | |
| 6,517,566 B1 | 2/2003 | Hovland et al. | |
| 6,659,938 B1 | 12/2003 | Orlowski et al. | |
| 6,705,987 B2 | 3/2004 | Anderson et al. | |
| 6,740,098 B2 | 5/2004 | Abrams et al. | |
| 6,905,459 B2 | 6/2005 | Humphries, Jr. | |
| 6,964,643 B2 | 11/2005 | Hovland et al. | |
| 7,083,570 B2 | 8/2006 | Bonthuys | |
| 7,141,055 B2 | 11/2006 | Abrams et al. | |
| 7,572,220 B2 | 8/2009 | Nan | |
| 7,588,533 B2 | 9/2009 | Drysdale | |
| 8,075,473 B2 | 12/2011 | Rudi | |
| 8,137,262 B2 | 3/2012 | Osbon et al. | |
| 8,382,656 B1 | 2/2013 | Brown | |
| 8,500,626 B2 | 8/2013 | Hovland et al. | |
| 8,998,796 B2 | 4/2015 | Green | |
| 9,265,750 B1 | 2/2016 | Benckini | |
| 2005/0033113 A1 * | 2/2005 | Bonthuys | A61F 5/41 600/38 |
| 2015/0164678 A1 * | 6/2015 | Lee | A61F 5/41 600/38 |

OTHER PUBLICATIONS

El-Sakka, Ahmed, Reversion of penile fibrosis: Current information and a new horizon, Arab J. of Urology (2011);9:49-55.

Molodysky, Eugen et al., Penile vascular surgery for treating erectile dysfunction: Current role and future direction, Arab J. of Urology (2013); 11:254-266.

Raina, R. et al., Early use of vacuum constriction device following radical prostatectomy facilitates early sexual activity and potentially earlier return of erectile function, Intl. J. of Impotence Research (2006);18:77-81.

Trepat, Xavier et al., Viscoelasticity of human alveolar epithelial cells subjected to stretch, Am. J. Physiol. Lung Cell Mol. Physiol. (2004);287:L1025-L1034.

The Ohio State University Comprehensive Cancer Center—Arthur G. James Cancer Hospital and Richard J. Solove Research Institute, ED Treatment with Manual Vacuum Erection Device (2016), 2 pages.

Wagner, Oliver I. et al., Softness, strength and self-repair in intermediate filament networks, Exp. Cell Res. (2007);313(10):2228-2235.

Wang, Ning, Mechanical Interactions Among Cytoskeletal Filaments, Hypertension (1998);32:162-165.

Wang, Ning, May the force be with you, The Scientist (Feb. 2017);31(2):44-49.

Yuan, J. et al., Review: Vacuum therapy in erectile dysfunction—science and clinical evidence, Intl. J. of Impotence Res. (2010);22:211-219.

PRI, Public Radio International, Using Mechanics To Stretch The Boundaries Of Cell Biology (Jan. 12, 2018), broadcast transcript, 7 pages.

Iacono, Fabrizio et al., Testosterone deficiency causes penile fibrosis and organic erectile dysfunction in aging men. Evaluating association among Age, TDS and ED, BMC Surgery (2012);12(Suppl1):S24, 5 pages.

Lin, Haocheng et al., The science of vacuum erectile device in penile rehabilitation after radical prostatectomy, Transl. Androl. Urol. (2013); 2(1):61-66.

* cited by examiner

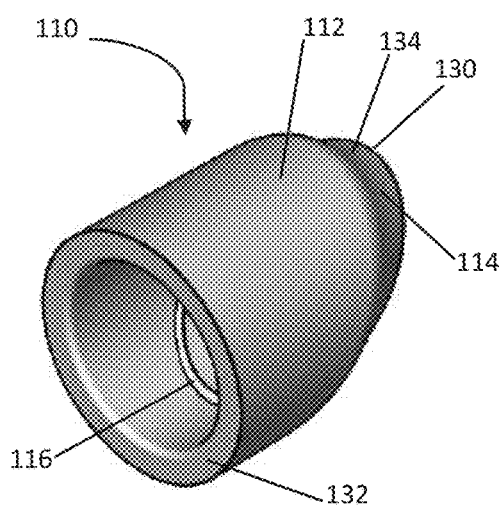
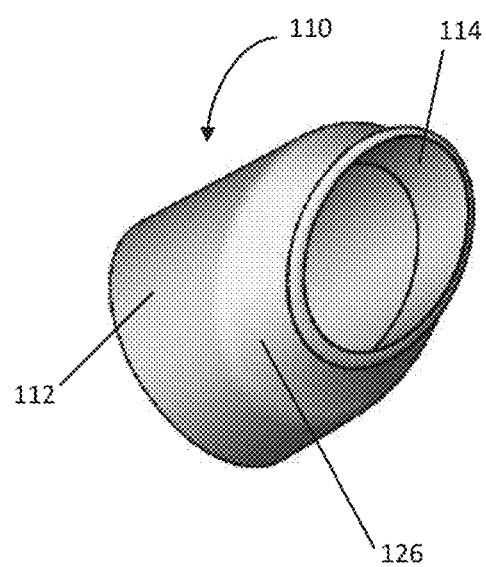
Figure 1
Figure 2
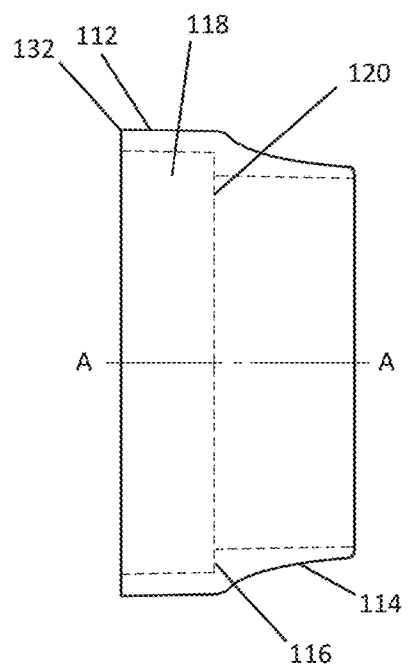
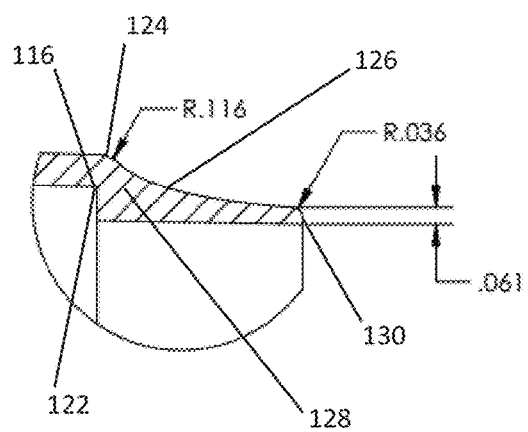
Figure 3
Figure 4

APPARATUS AND METHODS FOR TREATING VENOUS OCCLUSIVE DISORDERS

CROSS-REFERENCE TO RELATED APPLICATIONS

This application claims benefit under 35 U.S.C. 119(e) to U.S. Provisional Patent Application No. 62/672,017 entitled, "Apparatus and Methods for Treating Venous Occlusive Disorders" and filed on 15 May 2018, the contents of which are incorporated herein in their entirety for all purposes.

FIELD

Inventive concepts provide apparatus, methods and systems that utilize a soft (non-rigid), removable extension member adapted for treating venous occlusive disease through therapeutic application of vacuum. Inventive concepts can be used to treat, restore, or maintain tissue. Embodiments also include apparatus, methods and systems for use in connection with vacuum devices, for increasing clitoral and cavernosal tumescence.

BACKGROUND

Occlusion of blood vessels supplying a tissue can cause a decrease in blood flow inside the tissue, resulting in changes within the tissue, and ultimately, tissue damage or even necrosis. Blockage of even very small veins within a tissue can have significant effects. Occlusion can result from age, use of pharmaceuticals during therapy, radiation therapy, surgery, injury, and the like.

As people age, blood flow is often diminished to the genitalia. Diminished blood flow to the genitalia and related medical conditions can cause situations where normal physiological events that cause cell stretching within the genital tissues (e.g., caverosa) does not occur. As a result, cell stasis allows actin and microtubule growth and cell stiffness increases.

When cells are not stretched, various physiological changes can occur. For example, intracellular filament growth can occur from lack of cell stretching. These intracellular growths progress during stasis and ultimately connect from the cell nucleus to integrins in the cell membrane. The integrins in the cell membrane also connect to the extracellular matrix. With time, individual cells become increasingly stiff and non-pliable. Connection of contiguous cells through intracellular and extracellular structures over long range leads to various disease states. For example, soft tissue that is not pliable can cause coronary artery disease, erectile dysfunction, female sexual disorder, peripheral artery disease, and venous disease.

Several types of fibers grow within cells, including intermediate filaments, actin filaments, and microtubules. Intermediate filaments can stretch up to three times their original length and strengthen with deformation. Actin filaments and microtubules increase cell stiffness as they grow to connect the cell nucleus with the cell wall. Stretching cells, even small amounts, cause actin filaments and microtubules to break apart and result in decreased cell stiffness.

Study of the stress/strain relationship of human lung cells found changes in cell viscoelasticity with stretch. The researchers used vacuum force to stretch labeled cell boundaries under microscope imaging and found that the actin cytoskeleton plays a major role in cell mechanical response to stress. They also found that disruption of the actin filaments with latrunculin A in laboratory experiments caused a 10-fold drop in cell stiffness.

In vitro mechanical stimulation of mesenchymal stem cells has been shown to be effective in influencing cell differentiation and replication. Studies suggest that pluripotent cells become functionally mechanosensitive upon exit from the naive state. Thus, mechanical signals may become important in lineage specification of pluripotent cells. Mechanical cues can therefore be important in stem cell therapies.

Venous occlusive disorders in the female clitoris occur when the endothelial cells in the walls of the sinusoids are stiff and do not stretch to allow engorgement with blood flow. The function of natural stimulation of the clitoris requires two general steps, namely entry of blood into the clitoris via clitoral arteries, and retention of the blood via constriction of the veinal vessels to engorge the sponge like structure containing cavernous spaces for occupied blood.

Vacuum devices have been used to draw blood into the clitoris and cause an engorged and rigid clitoris. Current vacuum devices include a rigid or high durometer cylinder having a proximal end that contacts a patient. To achieve a vacuum with this design, the rigid cylinder must be pressed into the skin on the symphysis pubis. Pubic hair or even tissue trapped between the cylinder and skin can cause a vacuum leak and must be removed to achieve a vacuum. In some instances, surrounding tissue can be pulled into the cylinder, resulting in significant pain and potential injury.

SUMMARY

Inventive concepts relate to a soft extension member adapted for use with a rigid therapeutic vacuum chamber, for treatment of tissue. Such treatment can include repair, restoration, and/or maintenance of the tissue. In some aspects, inventive concepts can be utilized in connection with treatment of venous occlusive disorders. In some aspects, inventive devices, systems and methods can be used to increase clitoral and cavernosal tumescence by therapeutic application of vacuum to disrupt intracellular actin and microtubule formations. In some aspects, application of vacuum to soft tissue in vivo can cause expansion of cells in a manner that provides cellular stretching that can cause greater cell expansion; greater actin filament and microtubule breakage; increased cell viscoelasticity; and stimulation of stem cells. Stem cells are present throughout the body, and inventive methods can provide mechanical cues to activate stem cells already present within a tissue to be treated, thereby enhancing the treatment. Inventive concepts can provide these benefits while reducing or minimizing potential risks associated with conventional therapies.

Applications of inventive concepts will be readily appreciated in the field of treatment of venous occlusive disorders, particularly for treatment of sexual health disorders. In some aspects, inventive concepts can be used to increase clitoral and cavernosal tumescence. However, it will be readily appreciated that inventive concepts can be applied generally to treat any tissue within the body that can benefit from the mechanical stimulation using vacuum pressure described herein. In addition, combination therapies are contemplated. For example, methods described herein can be used in combination with introduction of stem cells, growth factors, and/or other therapeutic agents to the treatment site.

In some aspects, inventive devices for therapeutic application of negative pressure to a female clitoris comprise a soft extension member having a proximal end and a distal end;

the proximal end comprising a tissue contacting portion that is configured to receive a flaccid clitoris;

the distal end comprising a collar that is configured to be mounted onto an exterior surface of a vacuum erection device chamber;

a rim located between the collar and the tissue contacting portion, the rim being located on an interior surface of the soft extension member;

taper located between the collar and the tissue contacting portion, the taper being located on an exterior surface of the extension member; and an exterior rim located on the exterior surface of the extension member, between the collar and the taper.

Also contemplated are clitoral stimulation systems for increasing clitoral and cavernosal tumescence by vacuum therapy, the system comprising:

(a) a rigid vacuum chamber having an open proximal end, an interior surface and an exterior surface;

(b) a negative pressure generating device;

(c) a removable soft extension member comprising a proximal end and a distal end, the distal end comprising a collar that is configured to be mounted onto the open proximal end of the vacuum chamber, on the exterior surface, the proximal end comprising a tissue contacting portion that is configured to surround a body of a flaccid clitoris, and to form a clitoral seal between the vacuum chamber and the clitoral body.

Inventive methods further contemplate a device for therapeutic application of negative pressure to a tissue of the body, the device comprising a soft extension member having a proximal end and a distal end;

the proximal end comprising a tissue contacting portion that is configured to receive a tissue;

the distal end comprising a collar that is configured to be mounted onto an exterior surface of a vacuum device chamber;

a rim located between the collar and the tissue contacting portion, the rim being located on an interior surface of the soft extension member;

a taper located between the collar and the tissue contacting portion, the taper being located on an exterior surface of the extension member; and an exterior rim located on the exterior surface of the extension member, between the collar and the taper.

Illustrative tissues that can be treated include tissues affected by venous occlusive disorder, such as the female clitoris, male penis, and lower extremities affected by diabetic neuropathy, such as the feet or lower leg.

Dimensions of the tissue treatment device can be adapted based upon the tissue to be treated, using the disclosure herein as guidance.

Inventive concepts provide a soft extension member that is adapted to be used with commercially available vacuum cylinders, such as those used in vacuum clitoral stimulation therapy. The dimensions of the selected vacuum cylinder or chamber will depend upon the tissue to be treated and can therefore be modified using this s disclosure as guidance. Thus, discussion of inventive concepts will focus on applications in treatment of female sexual disorders for illustrative purposes. However, numerous additional applications will be apparent. For example, inventive concepts could also find use in treatment of other venous occlusion disorders, such as neuropathy.

In some implementations, inventive concepts provide methods of treating venous occlusive disease by application of a vacuum, the method comprising steps of:

(a) providing a vacuum assembly having a vacuum chamber and soft extension member, the vacuum chamber having a proximal end, a distal end, and an exterior surface, the soft extension member being removably mounted on the exterior surface of the proximal end of the vacuum chamber, the soft extension member including a tissue contacting portion that extends longitudinally away from the proximal end of the vacuum chamber;

(b) positioning the tissue contacting portion around a tissue to be treated;

(c) pumping air out of the vacuum chamber from the distal end to create a negative pressure within the vacuum chamber, thereby causing the tissue contacting portion to collapse around the tissue to be treated and create a vacuum seal;

(d) maintaining the negative pressure within the vacuum chamber for sufficient time to draw blood into the tissue to be treated and achieve a desired state of blood engorgement within the tissue;

(e) releasing the pressure within the vacuum chamber;

(f) repeating steps (c) through (e) to cycle the pressure within the vacuum chamber between a negative pressure state and a release state, for a desired number of cycles to achieve a therapeutic treatment course; and (g) completely removing the device from the patient.

During therapeutic use of the inventive concepts, vacuum pressure is increased to draw blood into the target tissue, then released, then vacuum is applied again. This repetition of vacuum application can produce maximum radial and longitudinal forces on the cells to break actin filaments and microtubules that cause cell stiffness, and/or s influence differentiation and/or replication of stem cells.

Also provided are methods for increasing clitoral and cavernosal tumescence comprising steps of:

(a) providing a vacuum erection assembly having a vacuum chamber and a soft extension member, the vacuum chamber having a proximal end, a distal end, and an exterior surface, the soft extension member being removably mounted on the exterior surface of the proximal end of the vacuum chamber, the soft extension member including a tissue contacting portion that extends longitudinally away from the proximal end of the vacuum chamber;

(b) positioning the tissue contacting portion around a body of a patient's clitoris;

(c) pumping air out of the vacuum chamber from the distal end to create a negative pressure within the vacuum chamber, thereby causing the tissue contacting portion to collapse around the body of the patient's clitoris and create a vacuum seal;

(d) maintaining the negative pressure within the vacuum chamber for sufficient time to draw blood into the clitoris and achieve a desired state of clitoral engorgement;

(e) releasing the pressure within the vacuum chamber;

(f) repeating steps (c) through (e) to cycle the pressure within the vacuum chamber between a negative pressure state and a release state, for a desired number of cycles to achieve a therapeutic treatment course; and (g) completely removing the device from the patient.

Optional steps include the following. A lubricant can be applied to the tissue prior to treatment. Negative pressure can be gradually increased during steps (c) through (f). Therapeutic agents can be administered to the treatment site in combination with inventive methods. Such combination treatments can include stem cells, growth factors and the like.

Aspects of the invention will now be described in more detail.

BRIEF DESCRIPTION OF THE FIGURES

The disclosure may be more completely understood in consideration of the accompanying drawings, in which:

FIG. 1 is a perspective view of a soft extension member in accordance with an embodiment of the invention;

FIG. 2 is a perspective view of a soft extension member in accordance with an embodiment of the invention;

FIG. 3 is a side view of a soft extension member mounted to a vacuum cylinder in accordance with an embodiment of the invention;

FIG. 4 is a cross-section view along view line A-A of FIG. 3;

DETAILED DESCRIPTION

Figure 5:
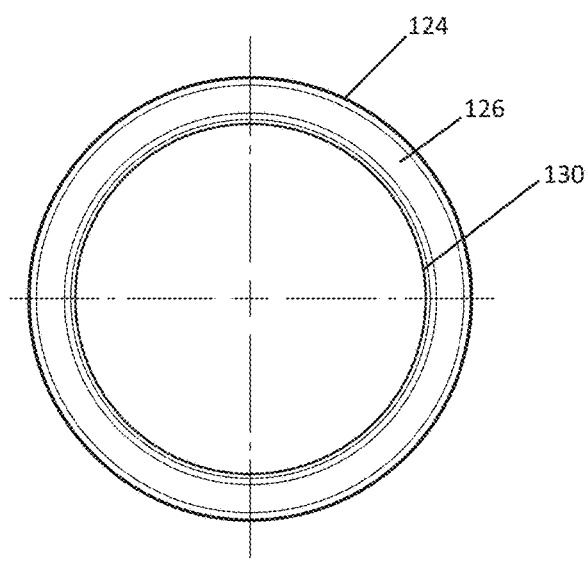
FIG. 5 an end view of a soft extension member, from the proximal end, in accordance with an embodiment of the invention.

In the following description, reference is made to the accompanying set of drawings that form a part hereof. The drawings are provided as illustration of several specific embodiments. Within the figures, like reference numbers are used to refer to comparable components across the various embodiments shown. It is to be understood that other embodiments are contemplated and may be made without departing from the scope or spirit of the present disclosure. The following detailed description, therefore, is not to be taken in a limiting sense.

Generally, when referring the devices herein, the "proximal end" refers to the end brought into proximity and/or contact with a user or patient during therapeutic operation, while a "distal end" is generally away from the body (e.g., torso) of the user or patient.

In some aspects, inventive methods involve use of a novel soft extension member in connection with vacuum apparatus for reducing intracellular and extracellular fibrotic connections that cause cell stiffness. Inventive concepts are particularly useful for therapeutic treatment of venous occlusive disease, such as such occlusive disease in the female clitoris.

Venous occlusive disease in the female clitoris occurs when the endothelial cells in the walls of the sinusoids are stiff and do not stretch to allow engorgement with blood flow. Repetitive therapeutic application of vacuum stretching and increasing vacuum level can cause breakage of intracellular connective actin filaments and microtubules, and can decrease cell stiffness in turn. Therapeutic cell stretching during moderate vacuum application allows full sinusoid engorgement and the resulting pressure causes the collapse of veins that pass between expanding sinusoids. Diminished venous flow traps blood within the cavernosa to allow full clitoral engorgement.

Therapeutic vacuum application reduces cell stiffness and increases tissue elasticity of the female clitoris when actin filament and microtubules have caused cell stiffness. Placement of a vacuum chamber over the affected tissue (e.g., clitoral) and application of a therapeutic level of vacuum causes radial expansion of the cells in the soft tissue within the cavernosa. Repetitive application of vacuum stretching and increasing vacuum level causes breakage of intracellular connective actin filaments and microtubules, and increases cell stiffness. The resulting effect of vacuum application is increased elasticity of clitoral tissues as cell stiffness is reduced.

Inventive concepts provide methods of increasing clitoral cavernosal tumescence by therapeutic application of a vacuum to disrupt intracellular actin and microtubule formations. As used herein, "therapeutic application" of vacuum means application of a negative pressure at levels and/or duration sufficient to treat a tissue and achieve a desired treatment outcome, such as increased blood flow, or increased tumescence, for example. In turn, a "therapeutic treatment course" can include a period of negative pressure, followed by a period of released pressure (a "cycle"), wherein this pattern of negative pressure-release is repeated a desired number of times, and for a desired total amount of time, to achieve a therapeutic effect. A "therapeutic level" generally refers to an amount in a range within which a positive outcome is expected to be achieved without causing any significant adverse effects in the patient. It will be appreciated that a "therapeutic level" can refer to any treatment parameter discussed herein, such as pressure level, cycle length; total treatment duration, and/or dosage of therapeutic agent. These therapeutic parameters are typically determined by a physician, during treatment of a patient, and thus differ according to the patient and treatment site.

Novel soft extension members described herein can be easily applied to commercially available vacuum chambers (such as cylinders) utilized in clitoral stimulation therapy.

Inventive extension members can be made of a unitary material that is easy to use, cost effective; and adaptable to existing technologies. The soft extension is fabricated of a low durometer elastomeric material, such as silicone, C-Flex® (commercially available from Saint-Gobain Performance Plastics Corporation), or other elastomer blends. Suitable materials to fabricate the extension member are soft materials that easily collapse under negative (e.g., vacuum) pressure. The material can have a low durometer, such as in the range of about 4 to about 50 Shore A, or about 4 to about 30 Shore A, or about 4 to about 20 Shore A.

FIGS. 1 and 2 illustrate a soft extension member 110 in accordance with inventive concepts. Generally speaking, soft extension member 110 includes a distal end 132 and a proximal end 134, the proximal end terminating in proximal tip 130. Soft extension member 110 includes a first collar portion 112 sized to fit over a rigid cylindrical vacuum chamber, and a second portion that extends longitudinally away from the collar portion, is tapered from the collar 112 and forms a tissue contacting portion 114 of the extension member 110. As illustrated in FIG. 1, the outer diameter of collar 112 is larger than the outer diameter of tissue contacting portion 114. Likewise, as illustrated in FIG. 2, the inner diameter of the collar 112 is larger than the inner diameter of the tissue contacting portion 114. An intermediate portion defining a rim 116 on the interior face, and a taper 126 at an exterior face, is located between the collar 112 and tissue contacting portion 114. Features of interior rim 116 and exterior taper 126 will be discussed in more detail below.

Soft extension member 110 provides a novel device, system and corresponding method for increasing clitoral and cavernosal tumescence by application of negative pressure (such as a vacuum). In accordance with inventive principles, the soft extension member is removable and reusable—that is, it is easily removed after a treatment course by a patient without use of additional tools. The soft extension member is fabricated from materials that make it easy to mount onto standard vacuum chambers and remove from the chamber once a therapeutic treatment course has been completed. At the same time, fabrication materials are durable enough to withstand treatment pressures; be easily mounted onto, and removed from, vacuum chambers; be easily cleaned; and be reusable for multiple treatment courses. In some aspects, inventive soft extension members can provide a patient-friendly, gentle therapeutic device and system. The tissue contacting portion 114 is the area of the device that contacts the patient. This portion of the device is soft and elastic, so that it reduces risk of tissue damage and/or discomfort during therapeutic use.

FIG. 3 illustrates a soft extension member 110 mounted on a vacuum chamber 118. Vacuum chamber includes a distal end adapted for connection to a device for creating negative pressure, such as a vacuum (not shown), a proximal end 120 that faces a patient in use, and an inner surface and an exterior surface. Soft extension member 110 is mounted at the proximal end 120 of the vacuum chamber 118, thereby forming a soft tissue contacting area that extends longitudinally in a proximal direction away from the vacuum chamber 118. When installed on a vacuum chamber 118, collar 112 of the extension member 110 is disposed over a portion of the exterior surface of the vacuum chamber 118.

As shown, soft extension member 110 does not extend into the interior space of the vacuum chamber 118. Rather, soft extension member 110 is mounted onto the exterior surface of the vacuum chamber 118 and extends in a proximal direction parallel to the longitudinal axis of the vacuum chamber. In this way, soft extension member 110 does not substantially obstruct the proximal opening of vacuum chamber 118, or significantly reduce the inner diameter of the assembly (vacuum chamber plus soft extension member) at the proximal end 120 of the vacuum chamber 118.

To mount soft extension member 110 onto the vacuum chamber 118, the material of the collar 112 is manually stretched and pulled over the exterior of the vacuum chamber until the interior rim 116 abuts the proximal end 120 of the vacuum chamber. The elastic material used to fabricate soft extension member 110 is easily stretched to fit around and conform to the exterior of a chosen vacuum chamber 118. While vacuum chamber 118 is illustrated as a cylinder, it is understood other shapes can be used as well, depending upon the tissue to be treated. Soft extension member 110 can be easily adapted to fit around and conform to any variety of shapes of a chosen vacuum chamber. Once the collar of the extension member 110 is located around the proximal end 120 of vacuum chamber 118, the collar is released, and the collar collapses to wrap tightly around the proximal end 120 of the vacuum chamber. The elastic recovery of the extension member 110 keeps the extension member in place around the exterior proximal end of a vacuum chamber during use. In accordance with this aspect, the interior surface of the collar 112 of soft extension member 110 engages the exterior surface of the vacuum chamber 118 to form a snug connection therebetween.

Tissue contacting portion 114 of soft extension member 110 extends from the proximal end of the rigid vacuum chamber 118 and provides a soft, flexible area for subsequent application to a site of treatment, for example, the body of a user's clitoris. Soft extension member 110 can be inserted over the exterior of a vacuum chamber 118 until the proximal end 120 of the vacuum chamber 118 seats onto the interior rim 116 of the soft extension 110. The resulting assembly of soft extension member 110 mounted on the exterior surface of vacuum chamber 118 provides a soft, non-rigid, conformable user contact surface at tissue contacting portion 114 of the extension member 110. The tissue contacting portion 114 is capable of forming a seal around an exterior of a treatment site, such as a clitoris. Advantageously, and due to the non-rigid material used to fabricate the soft extension member 110, this vacuum seal can be achieved rapidly once a vacuum is applied to the system. Such rapid vacuum can reduce or eliminate undesirable characteristics of prior methods and apparatus.

Vacuum chamber 118 typically comprises a transparent plastic or equivalent material that is generally longitudinal, having a longitudinal axis. Vacuum chamber 118 has a first open end 120 which is generally circular or elliptical and adapted for introduction of a user's flaccid clitoris (i.e., proximal to the user). A second open end (not shown) is generally circular (or oval shaped) and adapted for introduction of negative pressure to vacuum chamber (i.e., distal to the user), as originating from a vacuum source.

Inventive soft extension members can be utilized in connection with any vacuum chamber typically used for treatment of a selected tissue. In some aspects, soft extension members are utilized in connection with vacuum chambers used in clitoral stimulation therapy. Such vacuum chambers can be fabricated of a sufficiently rigid material to withstand vacuum pressure. Illustrative materials for fabrication of vacuum chambers include polycarbonate or similar material.

Dimensions of the vacuum chamber can be varied according to the end use. For example, a vacuum chamber used for clitoral stimulation therapy can have a length in a range of about 35-50 mm, and an internal diameter in a range of about 18-25 mm. The particular dimensions of the vacuum chamber 118 can be varied to accommodate patient size. In turn, dimensions of the soft extension member 110 can be selected to fit around the proximal exterior end 120 of the vacuum chamber 118, and extend a suitable length in a proximal direction therefrom. The interior diameter of the soft extension member can be selected to surround the tissue to be treated, and yet avoid drawing any sensitive tissues or pubic hair into the vacuum that are undesired.

Vacuum chamber 118 can be fabricated from any suitable material, such as, for example, acrylic or vinyl tubing. Vacuum chamber 118 can be injection molded or printed using 3D printing.

Soft extension member 110 includes a collar portion 112 and tissue contacting portion 114. The collar 112 is adapted to be applied around the exterior proximal end of a vacuum chamber 118, and tissue contacting portion 114 extends in a proximal direction away from the vacuum chamber.

Soft extension member 110 is fabricated from any suitable material that can provide desired features, such as suitable strength to be stretched and maintained over the exterior proximal surface of a vacuum chamber 118 during application of vacuum, and flexibility to provide a rapid seal when vacuum is applied.

Soft extension member 110 is contacted to a patient's skin around the base of the clitoris, thereby surrounding the clitoris. When a vacuum is applied, the second portion collapses around the base of the clitoris and rapidly forms a vacuum seal. Vacuum can then be applied to increase clitoral and cavernosal tumescence Dimensions of the vacuum chamber can be varied according to the end use. For example, a chamber used in clitoral stimulation therapy can have a wall thickness in a range of about 0.025 inches to about 0.2 inches, or about 0.03 to about 0.125 inches. First open end (proximal end) 120 of the vacuum chamber 118 can be provided with a generally round inside diameter of about 0.5 to 0.7 inches, or about 0.55 to about 0.6 inches, and second open end (distal) can have a generally round, oval, or other shape (depending upon shape of the vacuum connection of the specific device).

When used to treat other venous occlusive disorders or disease, the particular vacuum chamber can be modified according to the tissue to be treated. For example, for treatment of neuropathy (e.g., diabetic neuropathy), the vacuum chamber can be designed to accommodate the target tissue, such as a foot or lower leg.

In addition, such vacuum therapy devices can be used with electrical or manually operated pump mechanisms, as desired. A pressure cycle adjustment may also be provided for causing the vacuum pressure to cycle between a set negative value and no vacuum, with an adjustable period of about 0.1 second to several seconds.

In accordance with inventive concepts, the soft extension member can provide one or more improvements over existing clitoral stimulation therapies. The operational efficiency of any vacuum tissue therapy depends greatly on the quality of the vacuum seal obtained between the apparatus (i.e., the vacuum chamber) and the patient (i.e., user). If a poor-quality vacuum seal is obtained, either due to a continuously low sealing effect, or due to any intermittent significant leakage problem, the entire vacuum therapy may be significantly compromised. Alternatively, the user may experience personal frustrations with a device that provides an improper seal (and therefore failed vacuum), which may lead to dissatisfaction with the therapy routine. Therefore, a quality vacuum seal between the device and the user can be important.

Another feature of the vacuum seal that can be important relates to the fit between an individual user's anatomical size and the opening of the vacuum chamber. A significant advantage of inventive soft extension members is that the extension member is fabricated of a material, and in a configuration, such that it can conform to an individual's anatomy. This reduces the chance that a user would have difficulty finding a vacuum therapy device of the right size. In contrast, current clitoral stimulation devices that utilize a rigid vacuum chamber do not provide this flexibility. If the vacuum chamber is too large relative to the user's anatomy, poor vacuum sealing can occur. Another undesirable side effect of current vacuum therapy is undesired vacuum intake, such as intake of excessive amounts of pubic hair (causing potential discomfort during application), or even intake of surrounding tissue. Inventive concepts reduce or eliminate these undesirable possibilities. Inventive concepts provide the ability to selectively treat a target tissue, without adversely impacting or affecting surrounding tissues that do not require treatment.

While discussion herein provides details of vacuum chambers used in connection with clitoral stimulation therapy, it will be readily understood that inventive concepts can be adapted to be used in connection with a variety of vacuum chambers (in a variety of shapes and dimensions) used for therapy.

Referring to FIG. 3, a side view of a soft extension member 110 installed onto a vacuum chamber 118 is illustrated. Soft extension member 110 includes a distal end 132 that is positioned around the exterior of a vacuum chamber 118. Collar 112 is mounted around the exterior proximal end of the vacuum chamber 118, until proximal end 120 of the vacuum chamber meets interior rim 116 of the soft extension member 110. Interior rim 116 thus provides a surface area where the vacuum chamber 118 abuts the soft extension member 110. This surface area can be beneficial in creating a vacuum seal during use.

As shown in FIGS. 3 and 4, when viewed externally, soft extension member 110 is designed to become progressively thinner with greater distance from the proximal end 120 of rigid vacuum chamber 118. These changes in material thickness and profile will now be discussed.

The exterior profile of the soft extension member 110 generally includes a wider distal portion (defined by collar 112), a taper 126, and a more narrow proximal portion (defined by tissue contacting portion 114). Transition from the collar 112 into taper 126 occurs at an exterior rim 124. Exterior rim 124 can provide advantages during installation of the soft extension member 110 over a vacuum chamber 118, as it can provide a surface against which a user can apply manual pressure to push extension member 110 over the exterior surface of vacuum chamber until a seated fit occurs between interior rim 116 and proximal end 120. Taper 126 can provide increased exterior surface area for application of such manual pressure during installation of the soft extension member 10 over a vacuum chamber. Thus, these two exterior features can cooperate with each other to provide advantageous features to the assembly.

As shown in the figures, soft extension member 110 extends in a proximal direction parallel to the longitudinal axis of the vacuum chamber 118. As illustrated, no portion of the soft extension member protrudes into, or is located within, the interior of the vacuum chamber 118. In this way, the soft extension member 110 does not enter into or obstruct the interior space of vacuum chamber 118 or the assembly (vacuum chamber with soft extension member mounted thereon). Soft extension member 110 thus extends the device proximally. At the same time, the inner diameter at the proximal tip of soft extension member is approximately the same as the inner diameter of the vacuum chamber to which the soft extension member is mounted. This feature can be seen in FIGS. 7 and 9, wherein vacuum chamber 118 is shown with inner diameter D. The inner diameter of soft extension member 110 at proximal tip 130 is represented by dimension E. In the embodiments shown, this represents a reduction in diameter of approximately 4% and 12%, respectively. In some embodiments, the soft extension member 110 has an inner diameter E at proximal tip 130 that is at least 80%, or at least 85%, or at least 90% or at least 95% of the inner diameter D of vacuum chamber 118. Put another way, mounting the soft extension member 110 onto vacuum chamber 118 does not significantly reduce the inner diameter of the assembly. This can provide significant features to the assembly, as discussed herein.

Looking at the soft extension member 110 itself, the overall inner and outer diameter of the soft member progressively decreases from its distal to its proximal end. As shown in FIG. 3, the inner diameter of collar 112 is greater than the inner diameter of tissue contacting portion 114. This occurs because collar 112 is sized to fit over the exterior surface of a vacuum chamber, whereas the tissue contacting portion is sized to fit a patient's anatomy at a treatment site. This diameter reduction occurs at interior rim 116. As illustrated in FIG. 4, interior rim 116 can include a 90° angle 122 for seating against the proximal end 120 of the vacuum chamber, thereby providing a seal fit. It will be readily understood that fabricating the device with a 90° angle at 122 can provide advantages during fabrication of the device. However, angles other than 90° can also be used, if desired. The angle at 122 can be selected to conform to the shape and/or angle at proximal end 120 of a vacuum chamber.

Dimensions of the interior rim 116 can be selected to provide advantages. In some embodiments, interior rim 116 can have a length that is approximately equal to the thickness of the walls of vacuum chamber 118. In this aspect, the interior surface of tissue contacting portion 114 can form a near seamless transition from the vacuum chamber 118, which can help avoid areas that could compromise a vacuum pressure and/or damage tissue (for example, by pinching or impinging on tissue). In this aspect, the vacuum assembly (vacuum chamber 118 plus soft extension member 110) can include an interior diameter that does not substantially decrease from the proximal end 120 of vacuum chamber 118.

As illustrated in FIG. 3, the outer diameter of collar 112 is also greater than the outer diameter of tissue contacting portion 114. This diameter reduction occurs at exterior taper 126. FIG. 4 illustrates a cross section of soft extension member 110 along view line A-A from FIG. 3. FIG. 4 shows the reduction of the soft extension member inner diameter at 90° angle 122 of interior rim 116, and outer diameter at exterior taper 126.

As shown, thickness of soft extension member 110 varies along its length. Collar 112 is provided with a first thickness that remains relatively constant from the distal end 132 to the interior rim 116. In contrast, tissue contacting portion 114 is provided with a second thickness that is less than the thickness of collar 112. The larger thickness of collar 112 can provide advantages such as increased strength at collar 112 for mounting and retention at the proximal end 120 of vacuum chamber 118. In an illustrative embodiment, collar 112 can have a thickness in a range of about 0.2 to about 0.4 inches, or about 0.2 to about 0.3 inches.

Thickness of the tissue contacting portion progressively decreases in a proximal direction, from the shoulder 128 and along the exterior taper 126, to a proximal tip 130. Proximal tip 130 is thus the thinnest portion of the soft extension member 110. In some aspects, thickness at the proximal tip 130 can be in a range of about 0.01 to about 0.05 inches. In some implementations, thickness of proximal tip 130 is sufficient to minimize the risk that it can be pulled into the interior of the vacuum chamber when a vacuum pressure is applied. Proximal tip can be provided in any desired shape, including rounded or blunt.

In use, when the soft extension member 110 is seated at the proximal end 120 of a vacuum cylinder 118, the assembly can be placed over the clitoris of a user along the body of the clitoris, in proximity to the base. The collar 112 is thus seated circumferentially around the exterior of the vacuum cylinder, and tissue contacting portion 114 is seated at or near the base of the clitoris, and along the body. When vacuum is applied, the tissue contacting portion 114 collapses circumferentially onto the body of the clitoris and easily forms a vacuum seal. Thickness of tissue contacting portion 114 can be selected to provide desired features, such as sufficient durability and strength to withstand vacuum pressure without folding in upon itself and thereby preventing formation of a vacuum seal; and/or sufficient flexibility to rapidly form a vacuum seal upon application of the vacuum.

As also illustrated in FIG. 4, inclusion of interior rim 116 and exterior taper 126 creates a shoulder area 128 of increased material thickness. This increased thickness can provide advantages, such as formation of a durable fit where soft extension member 110 seats against the end portion 120 of the vacuum chamber, and material strength to withstand force applied when a user mounts the soft extension member 110 to the vacuum chamber, and pressure of vacuum once it is applied. In some aspects, the thickness at shoulder 128 can be in a range of about 0.4 to about 0.5 inches at its maximum.

FIG. 5 illustrates an end view of the soft extension member 110, looking through the extension member 110 from the proximal (patient contacting) end. Proximal tip 130, exterior taper 126 and exterior rim 124 are shown. In some embodiments, the proximal tip 130 and/or the vacuum chamber proximal end 120 can be flared, if desired.

Figure 6:
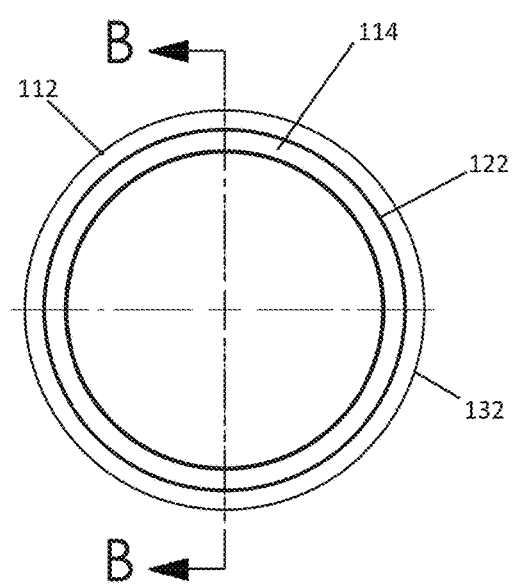
FIG. 6 is an end view of a soft extension member, from the center of the distal end, in accordance with an embodiment of the invention.
Figure 7:
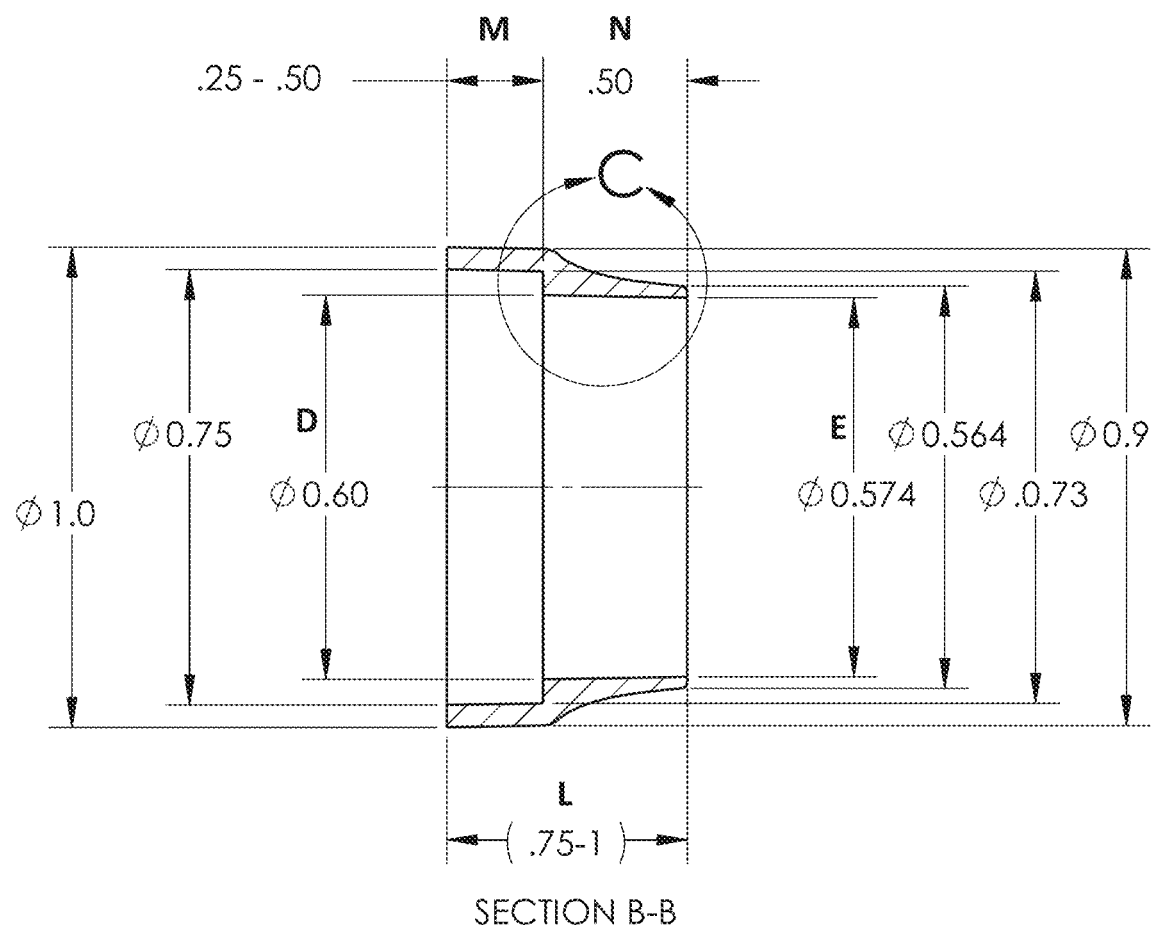
FIG. 7 is a partial cross-section view along view line B-B of FIG. 6.

FIG. 6 illustrates an end view of the soft extension member 110, looking through the center of the extension member 110 from the distal end. The demarcation between collar 112 and tissue contacting portion 114 is visible at the right angle 122 defined at the interior rim of the apparatus. FIG. 7 is a cross sectional view taken along line B-B of FIG. 6. In the particular embodiment illustrated, soft extension member 110 is shown having an overall length L of 0.75 to 1 inch, wherein the collar 112 has a length M of 025 to 0.5 inches, and tissue contacting portion 114 has a length N of 0.5 inches.

Referring to FIG. 7, soft extension member 110 can have an overall length suitable for use. When used in connection with vacuum chambers for VED, overall length L can be in a range of 0.7 to 1.25 inches, or 0.75 to 1 inch, for example. Relative length of the collar 112 versus the tissue contacting portion 114 of the soft extension member 110 can be varied to suit the particular device and application. When used in connection with a VED for application to a female clitoris, collar 112 can have a length M in a range of 0.2 to 0.5 inches, or 0.25 to 0.5 inches, and tissue contacting portion 114 can have a length N in a range of 0.25 to 0.6 inches, or 0.25 to 0.5 inches. In some aspects, the length M can be equal to length N; alternatively, M can be greater than N, or N can be greater than M. The length M of collar 112 can be selected to provide sufficient surface area between the exterior surface of vacuum chamber 118 and soft extension member 110 to provide a stable device for use. Length N of tissue contacting portion 114 can be selected to provide sufficient surface area to form a comfortable vacuum seal along the body of a patient's clitoris during use, but not so long that it could be pulled into the interior of the vacuum cylinder when a vacuum pressure is applied, or would be difficult to break the vacuum seal once a therapy session is completed.

It will be readily appreciated the dimensions illustrated in FIG. 7 can be easily adapted to modify the soft extension member 110 for use with any vacuum chamber, and for virtually any vacuum therapy and/or tissue treatment desired.

The collar 112 of soft extension member 110 has an inner diameter approximately equal to the outer diameter of the vacuum chamber. Accordingly, a snug fit can be provided between the inner surface of collar 112 and the exterior surface of vacuum chamber 118 to form a tight seal even prior to a vacuum condition being formed within vacuum chamber 118. Interior rim 116 can contribute to this tight seal by providing increased surface area for contact between soft extension member 110 and vacuum chamber 118. Soft extension member 110 is fabricated of a material that allows it to be removably mounted to the vacuum chamber for use, without requiring significant stretching or deforming the soft extension member 110 by hand or with additional tools.

Once mounted onto the proximal end 120 of a vacuum chamber 118, the inner diameter of the tissue contacting portion 114 of soft extension member 110 is approximately equal to, or slightly less than, the inner diameter of vacuum chamber 118 prior to application of a vacuum condition. In some implementations, the inner diameter of tissue contacting portion 114 is substantially equal to, or slightly greater than, the exterior diameter of a flaccid clitoris. This configuration allows a user to easily apply the device to the user's clitoris. Once a vacuum is applied to the system, the tissue contacting portion 114 rapidly collapses around the circumference of the clitoris, forming a vacuum seal.

Soft extension member 110 can be fabricated as a unitary piece. Illustrative materials include silicone or similar soft (e.g., elastomeric) material that easily collapses under vacuum pressure. Exemplary methods of manufacture considered suitable to fabricate the soft extension member 110 include extrusion processes, molding processes, 3D printing, and any other method considered suitable for the particular material chosen.

Figure 8:
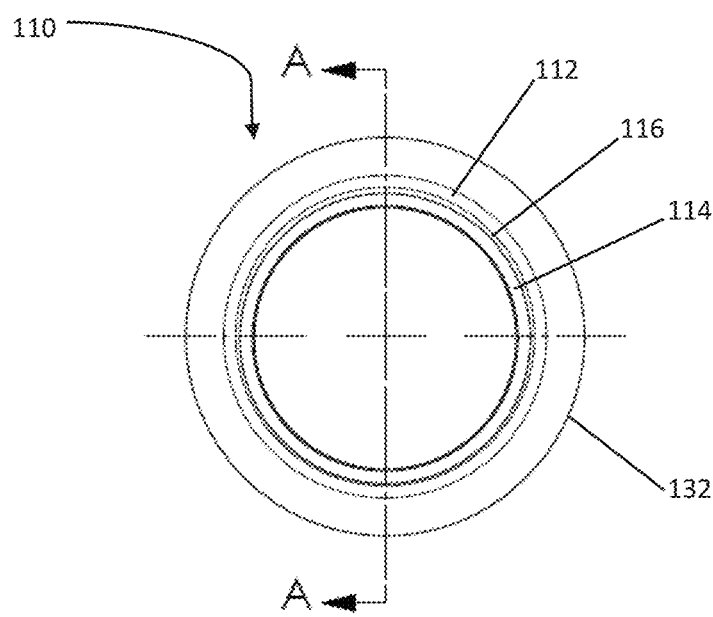
FIG. 8 is an end view of a soft extension member, from the distal end, in accordance with an embodiment of the invention.
Figure 9:
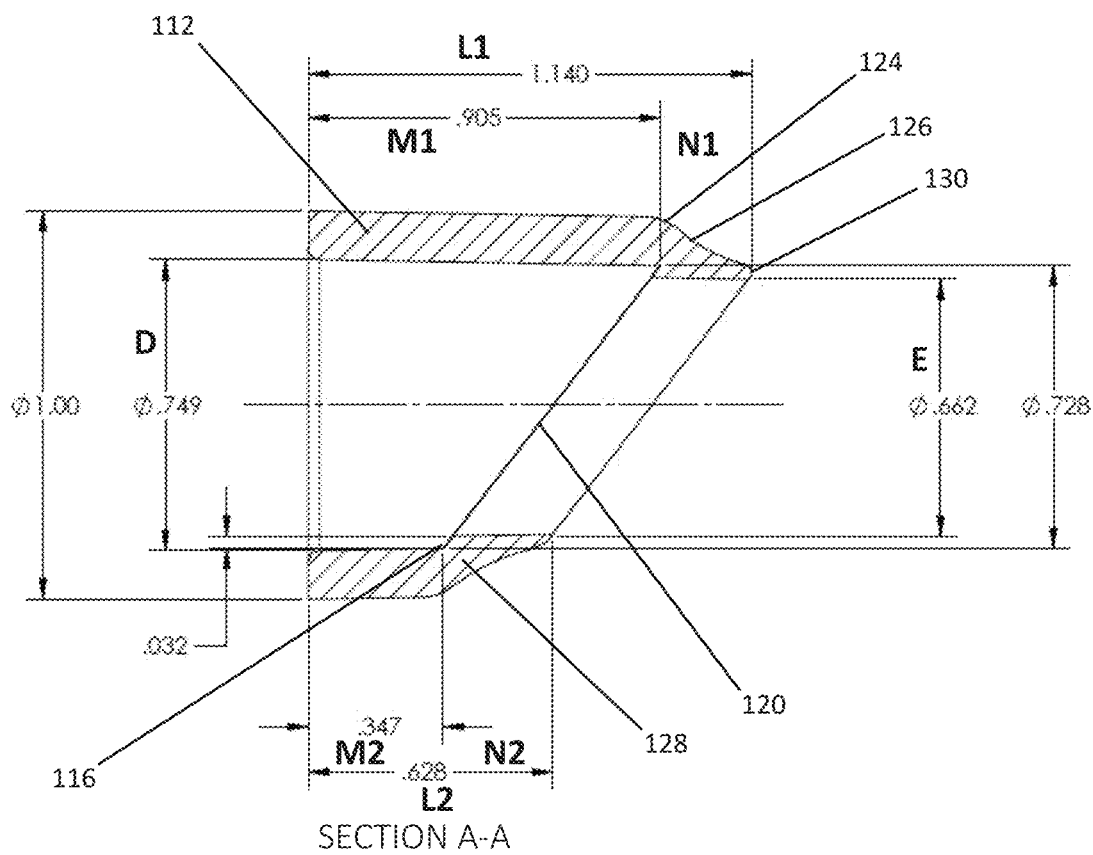
FIG. 9 is a partial cross-section view along view line A-A of FIG. 8.

Referring to FIGS. 8 and 9, one embodiment of soft extension member 110 is illustrated. FIG. 8 illustrates an end view of a soft extension member 110, looking through the center of the extension member 110 from the distal end 132. The demarcation between collar 112 and tissue contacting portion 114 is visible at interior rim 116 defined at the interior rim of the apparatus.

FIG. 9 is a cross sectional view taken along line A-A of FIG. 8. In the particular embodiment illustrated, soft extension member 110 is shown having a single oblique face, similar to the configuration illustrated in FIGS. 1 and 2. As shown, soft tissue member 110 includes a portion having first length L1 that is longer than a portion having second length L2. The particular lengths L1 and L2 are selected to conform to the dimensions of a vacuum chamber 118 to which the soft extension member 110 is to be mounted, and/or the dimensions of a particular tissue to be treated. In this instance, vacuum chamber 118 includes an oblique face at its proximal end 120. In the illustrated embodiment, dimension L1 comprises a length of the collar 112, defined as M1 in the figure, and a length of the tissue contacting portion 114 defined as N1 in the figure. Likewise, dimension L2 comprises a length of the collar 112 defined as M2 in the figure, and a length of the tissue contacting portion 114 defined as N2 in the figure. In the embodiment shown, both the collar 112 and tissue contacting portion of L1 are longer than their counterparts of L2. In other words, each of the collar 112 and tissue contacting portion 114 can be independently adjusted to conform to the configuration at the proximal end 120 of vacuum chamber 118 and/or a tissue to be treated. This provides a soft extension member 110 that has a longer dimension along a selected portion of the member. Given the oblique face at the proximal end 120 of vacuum chamber 118, interior rim 116 is not provided as a right angle, but rather is determined by the angle of the bisecting plane. Soft extension member 110 can be provided in the shapes illustrated in the figures, and/or in any other irregular angle-cut cylindrical shape, and can be selected to conform to the dimensions of any vacuum chamber used for treatment and/or any treatment site.

Also illustrated in FIG. 9 is an embodiment wherein collar 112 is longer than tissue contacting portion 114. The relative length of collar 112 versus tissue contacting portion 114 can be adjusted depending upon such factors as the configuration of the vacuum chamber, material used to fabricate the extension member 110, and/or the tissue to be treated.

In some implementations, a method includes steps of placing the soft extension member 110 around an exterior surface of the proximal end 120 of a vacuum chamber 118. The inner diameter of the collar 112 of soft extension member 110 is substantially equal to the outer diameter of the vacuum chamber 118. Thus, a seal is formed and maintained between the inwardly facing surface of the soft extension member 110 and the exterior surface of the vacuum chamber 118. Once the soft extension member 110 is mounted onto the vacuum chamber 118, the assembly is placed around the body of a user's flaccid clitoris, so that the tissue contacting portion 114 of the soft extension member 110 surrounds the clitoral body near the base of the clitoris.

A vacuum pump, connected to the vacuum chamber second (distal) end, then applies a vacuum pressure to the interior of the vacuum chamber. When the pressure pump is operating, a pressure is created inside the chamber and exerted upon the tissue or extremity received within the vacuum assembly. The vacuum pressure draws blood into the tissue (e.g., clitoris), causing engorgement and rigidity. The vacuum pressure is applied in cycles, with periods of vacuum followed by release of vacuum, to allow sufficient clitoral tumescence. In these aspects, blood is drawn into the clitoris, then released, then vacuum is applied again. This repetition of vacuum application can produce maximum radial and longitudinal forces on the cells to break actin filaments and microtubules that cause cell stiffness. Once tumescence is achieved, the vacuum is maintained for a desired period of time, for example, about 2 minutes.

In some implementations, methods of increasing clitoral and cavernosal tumescence involve pumping air out of the vacuum chamber from the distal end to create a negative pressure within the vacuum chamber, thereby causing the tissue contacting portion to collapse around the body of the patient's clitoris and create a vacuum seal; maintaining the negative pressure within the vacuum chamber for sufficient time to draw blood into the clitoris and achieve a desired state of clitoral engorgement; and releasing the pressure within the vacuum chamber. These steps of creating the vacuum seal/maintaining negative pressure/releasing pressure can comprise a therapeutic cycle. This cycle can be repeated a desired number of times to achieve a therapeutic treatment course. Optionally, once tumescence is achieved, the vacuum can be maintained for a desired (e.g., extended) period of time, before final release of vacuum.

Once a therapeutic treatment course has been completed, the vacuum is released, and the device is completely removed from the patient. In this aspect, no device parts remain on the patient.

At the desired time, the user then releases the vacuum pressure, and removes the device. Typical vacuum control systems include a vacuum release valve or button for this purpose. Optionally, the user can manually manipulate the tissue at the tissue contacting portion of the device to release the vacuum. For example, the user could slightly move or compress the tissue to release the contact between the device and clitoral body, if needed.

In an illustrative method, the soft extension is used in typical clitoral stimulation therapy.

When creating a seal between the soft extension member and a flaccid clitoris, it can be advantageous to apply a lubricant, such as KY® Jelly or similar product, for example, around the interior surface of the soft extension member and/or the body of the clitoris. Applying a lubricant can, in some aspects, reduce friction and establish an improved vacuum seal between the device and clitoris.

Inventive concepts further provide methods for treating tissue that involve repair, restoration, and/or maintenance of the tissue. Illustrative applications include treatment of neuropathy. Thus, in some aspects, inventive concepts provide methods of treating venous occlusive disease by application of a vacuum, the method comprising steps of: (a) providing an assembly comprising a vacuum chamber and soft extension member, the vacuum chamber having a proximal end, a distal end, and an exterior surface, the soft extension member being removably mounted on the exterior surface of the proximal end of the vacuum chamber, the soft extension member including a tissue contacting portion that extends longitudinally away from the proximal end of the vacuum chamber; (b) positioning the tissue contacting portion around a tissue to be treated; (c) pumping air out of the vacuum chamber from the distal end to create a negative pressure within the vacuum chamber, thereby causing the tissue contacting portion to collapse around the tissue to be treated and create a vacuum seal; (d) maintaining the negative pressure within the vacuum chamber for sufficient time to draw blood into the tissue to be treated and achieve a desired state of blood engorgement within the tissue; (e) releasing the pressure within the vacuum chamber; (f) repeating steps (c) through (e) to cycle the pressure within the vacuum chamber between a negative pressure state and a release state, for a desired number of cycles to achieve a therapeutic treatment course; and (g) completely removing the device from the patient.

Optionally, step (f) comprises repeating steps (c) through (e) to cycle the pressure within the vacuum chamber between a negative pressure state and a release state, for a desired number of cycles to achieve a therapeutic treatment course for treatment of neuropathy. Optionally, the method further comprises a step of maintaining the negative pressure for an extended time before final release of pressure within the vacuum chamber. Duration of the final, extended period of negative pressure can be selected to provide the desired effect on the tissue to be treated. In some embodiments, a lubricant, such as a medical lubricant, can be applied to the tissue to be treated. Illustrative medical lubricants include Surgilube® (commercially available from HR Pharmaceuticals, Inc. York, Pa.), K-Y Jelly, medicinal castor oil, or the like.

Optional features include any of the following. Methods can include combination therapy, wherein one or more therapeutic agents are administered to the patient before, during and/or after treatment. Exemplary therapeutic agents include, but are not limited to, stem cells (and/or other multipotent and/or pluripotent cells), growth factors, and the like. In some aspects, inventive methods can provide enhanced stem cell therapy, as the provision of mechanical stimulation (via application of vacuum) can provide mechanical cues that encourage stem, multipotent and/or pluripotent cells to differentiate at the treatment site.

Therapeutic agents can be administered in any desired manner, including direct injection at the treatment site, injection in an area proximal to the treatment site, or intravenous injection. For treatment of venous occlusive disorder in a female clitoris, intracorporal injection of stem cells may be advantageous.

In some implementations, a system for increasing clitoral and cavernosal tumescence includes a vacuum chamber, a negative pressure source secured to one end of the vacuum chamber, and a soft extension member removably mounted to the exterior surface of the vacuum chamber at a proximal end. The soft extension member includes a collar portion that sealingly engages the exterior surface of the vacuum chamber at is proximal end, and a second (tissue contacting) portion that is capable of forming a seal with a user's clitoris.

In some implementations, inventive concepts provide a stimulation therapy system for increasing clitoral and cavernosal tumescence by vacuum therapy, the system comprising: (a) a rigid vacuum chamber having an open proximal end, an interior surface and an exterior surface; (b) a negative pressure generating device; and (c) a removable soft extension member comprising a proximal end and a distal end, the distal end comprising a collar that is configured to be mounted onto the open proximal end of the vacuum chamber, on the exterior surface, the proximal end comprising a tissue contacting portion that is configured to surround a body of a flaccid clitoris, and to form a clitoral seal between the vacuum chamber and the clitoral body.

Optionally, the system can further comprise (a) a rim located between the collar and the tissue contacting portion, the rim being located on an interior surface of the soft extension member; (b) a taper located between the collar and the tissue contacting portion, the taper being located on an exterior surface of the extension member; and (c) an exterior rim located on the exterior surface of the extension member, between the collar and the taper.

Typical negative pressures can be within a safe level, such as up to about 400 mm Hg. Cyclic vacuum can be in a range of about 100 to about 400 mm Hg, or about 150 to about 300 mm Hg, or about 200 to about 250 mm Hg. Such pressures can be applied in cycles lasting a period of about 0.1 second to several minutes.

Because the soft extension member is provided over the exterior surface of a vacuum chamber, it is easily adaptable to a wide variety of vacuum therapy devices already on the market. The soft extension member is fabricated of a material that can stretch to accommodate different sizes and shapes of vacuum chambers, while not proving difficult to stretch for mounting. Inventive soft extension members are not seated within the interior of the vacuum chamber, which would limit size variance and tolerance. Because the soft extension member extends in a proximal direction from the rigid vacuum chamber, it provides a soft, pliable engagement surface for a patient. As noted herein, the soft extension member can provide a rapid vacuum seal.

Other advantageous features can include, for example, the ability to customize any commercially available vacuum chamber to an individual's anatomy. Further, the tissue contacting portion 114 of the soft extension member 110 collapses around and seals at the clitoral body, and not the abdomen. This reduces risk of pulling additional tissues into the vacuum, potentially causing pain and tissue damage. The soft extension member 110 creates a seal with both a vacuum chamber and a clitoris to which the soft extension member is secured without requiring extensive stretching or deformation of the extension member to mount it to either the vacuum chamber or the clitoris.

Because the inventive soft extension members are flexible, they are much more readily adaptable to changes in patient's needs.

Inventive soft extension members provide a cost-effective, disposable, easily adaptable device that can change with patient's needs. In some aspects, inventive devices can accommodate varying clitoral sizes and severity of condition. In some implementations, inventive soft extension members are reusable, and provide a single-patient, multiple use product. During the course of therapy, a patient can use a selected soft extension member multiple times, unless and until a different size is required during the overall therapy (for example, if clitoral size changes during the course of therapy).

More generally, inventive methods and systems provide enhanced treatment options due to the relatively uniform expansion of tissue caused by vacuum. In addition, the extent of tissue expansion is easily controllable by manipulating the level of vacuum pressure. This can provide advantages over uniaxial mechanical stretching techniques.

All publications and patents mentioned herein are hereby incorporated by reference to the same extent as if each individual publication or patent was specifically and individually indicated. The publications and patents disclosed herein are provided solely for their disclosure. Nothing herein is to be construed as an admission that any publication and/or patent is prior art.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained.

In the specification and in the claims, the terms "including" and "comprising" are open-ended terms and should be interpreted to mean "including, but not limited to . . . " These terms are broader than, and therefore encompass, the more restrictive terms "consistently essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

The invention claimed is:

1. A method of increasing clitoral and cavernosal tumescence comprising steps of:
    (a) providing a vacuum assembly comprising a vacuum chamber and soft extension member, the vacuum chamber having a proximal end, a distal end, and an exterior surface, the soft extension member being removably mounted on the exterior surface of the proximal end of the vacuum chamber, the soft extension member including a tissue contacting portion that extends longitudinally away from the proximal end of the vacuum chamber;
    (b) positioning the tissue contacting portion around a body of a patient's clitoris;
    (c) pumping air out of the vacuum chamber from the distal end to create a negative pressure within the vacuum chamber, thereby causing the tissue contacting portion to collapse around the body of the patient's clitoris and create a vacuum seal;
    (d) maintaining the negative pressure within the vacuum chamber for sufficient time to draw blood into the clitoris and achieve a desired state of clitoral engorgement;
    (e) releasing the pressure within the vacuum chamber;
    (f) repeating steps (c) through (e) to cycle the pressure within the vacuum chamber between a negative pressure state and a release state, for a desired number of cycles to achieve a therapeutic treatment course;
    (g) completely removing the vacuum assembly from the patient; and
    (h) administering stem cells to the patient.

2. The method of claim 1 further comprising a step of applying a lubricant to the clitoris prior to step (b).

3. The method of claim 1 wherein the negative pressure is in a range of 125 mm Hg to 300 mm Hg.

4. The method of claim 1 wherein step (f) comprises a therapeutic treatment course lasting 30 seconds to 15 minutes.

5. The method of claim 1 wherein negative pressure is gradually increased during step (c).

6. The method of claim 1 wherein step (h) is performed after the vacuum assembly is completely removed from the patient.

7. The method of claim 1 wherein step (h) is performed before the tissue contacting portion is positioned around the body of the patient's clitoris.

8. The method of claim 1 wherein step (h) comprises injection of the stem cells.

* * * * *